United States Patent [19]

Ladell et al.

[11] 4,074,132
[45] Feb. 14, 1978

[54] AUTOMATIC SINGLE CRYSTAL DIFFRACTOMETER

[75] Inventors: Joshua Ladell, Monsey, N.Y.; Gerald Kennedy Pitcher, Old Lyme, Conn.

[73] Assignee: North American Philips Corporation, New York, N.Y.

[21] Appl. No.: 717,372

[22] Filed: Aug. 24, 1976

[51] Int. Cl.² ............................................. G01N 23/20
[52] U.S. Cl. ................................. 250/277 R; 250/272
[58] Field of Search ............ 250/272, 273, 278, 277 R

[56] References Cited

U.S. PATENT DOCUMENTS

| 3,105,901 | 10/1963 | Ladell et al. | 250/277 R |
| 3,634,686 | 1/1972 | Sekita | 250/278 |
| 3,868,506 | 2/1975 | Ogiso | 250/278 |

Primary Examiner—Bruce C. Anderson
Attorney, Agent, or Firm—Frank R. Trifari; Carl P. Steinhauser

[57] ABSTRACT

A diffractometer for acquiring crystallographic data from single crystal having means to mount the crystal in the path of a beam of x-rays, a moveable detector and means to constrain the detector to move on an arc which rotates about a horizontal axis so that the detector is sequentially positioned along a line of the reciprocal lattice of the crystal.

6 Claims, 1 Drawing Figure

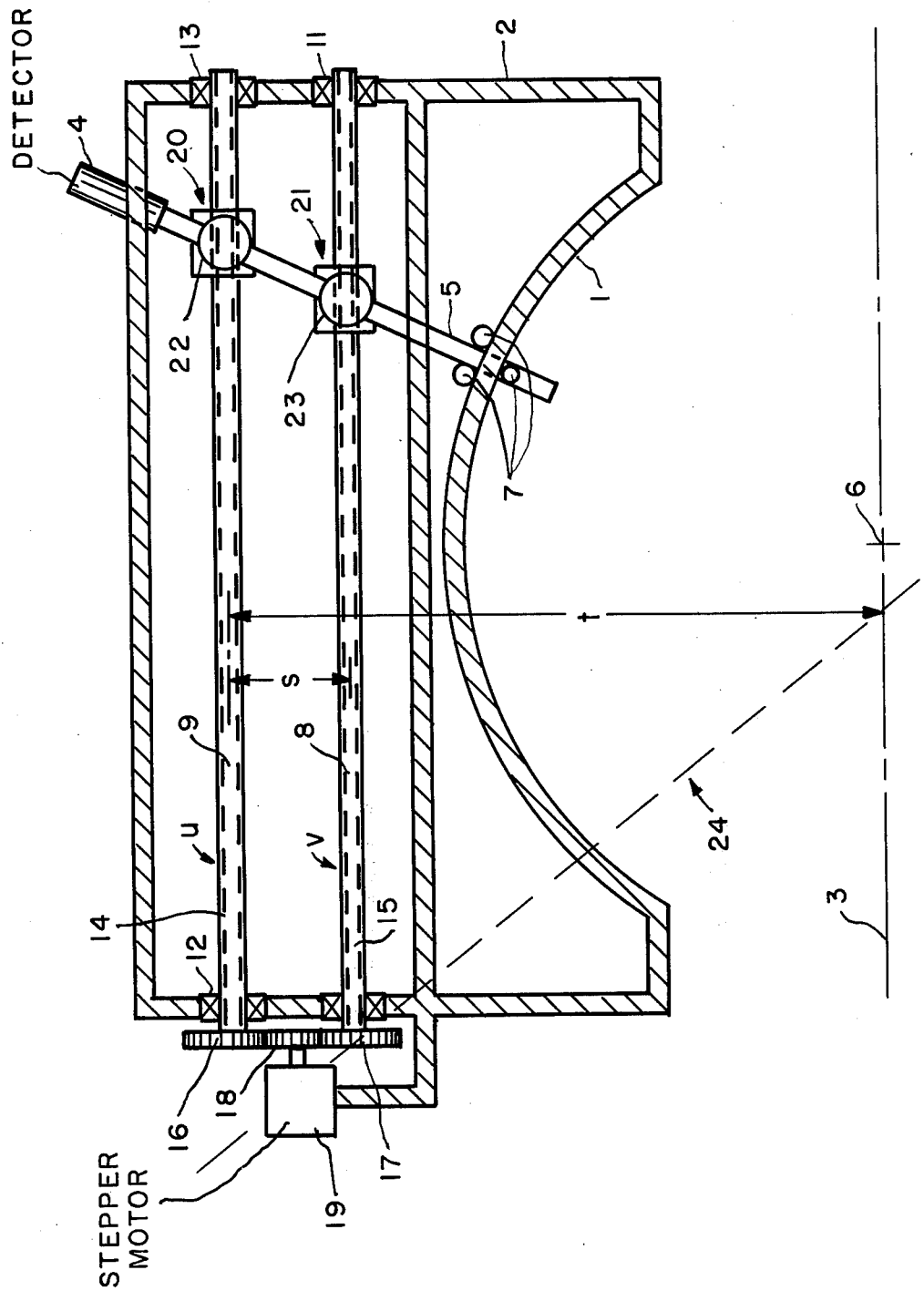

AUTOMATIC SINGLE CRYSTAL DIFFRACTOMETER

The invention relates to a diffractometer for automatically acquiring crystallographic data from a single crystal in which, as the crystal rotates, the detector is sequentially positioned along a line of the reciprocal lattice of the crystal.

A diffractometer of this type has been described in U.S. Pat. No. 3,105,901, and in an article by P. G. Cath and J. Ladell in the Philips Technical Review, Vol. 29, 1968, No. 6, pp. 165–185. In the devices there described, a model of the reciprocal lattice of the crystal is employed which is linked to a detector in such a manner as to successively execute the process of bringing reciprocal lattice points into the sphere of reflection while simultaneously providing that the detector be in its correct position to sense the diffraction effect when it takes place. The detector, there a scintillation detector, is constrained to move on an arc while the arc itself rotates about a horizontal axis.

It is an object of our invention to automate the detector rotation on the arc and thereby facilitate the collection of diffraction data.

This and further objects of the invention will appear as the specification progresses.

In accordance with the invention we provide a double lead screw linkage arrangement supported in a frame, which also supports the arc, by bearings which constrain translation and is driven by a common stepping motor. The center of arc is a given distance from the furtherest lead screw, the two lead screws being separated by a smaller distance. The detector is mounted on an arm which is coupled to both lead screws one end of the arm being moveably connected to the arc. The pitch of the respective lead screws is chosen so that the ratio of the pitches is such that it equals the quotient of the distance of the furtherest lead screw to the center of the arc divided by the difference between that distance and the distance separating the two lead screws. Thus, with the arm initially pointing to the center of the arc, it will always point to the center of the arc as the lead screws are rotated moving the detector arm.

The invention will be described in greater detail with reference to the accompanying drawing in which the sole FIGURE shows in section the detector movement constraining mechanism.

Referring to the drawing an arc 1 is mounted on a frame 2 for rotation about a horizontal axis 3. A detector 4 is mounted on an arm 5 to point initially at a point 6 on the horizontal axis of rotation. Arm 5 is rigidly connected at one end to arc 1 by three rollers 7.

A pair of lead screws 8 and 9 are mounted in bearings 10, 11, 12 and 13 respectively in frame 1 which constrain translation of the lead screws. Each of the lead screws terminate in shafts 14 and 15, respectively, which are rigidly connected to spur gears 16 and 17 respectively. These gears mesh with a gear 18 which, in turn, is driven by a stepper motor 19 supported by the frame.

The axis of lead screws 8, 9 are separated by a distance S while lead screw 9, the furtherest from the horizontal axis, is at a distance therefrom of $t$.

Nuts 20 and 21 moveable on lead-screws 8 and 9, respectively, support sliding swivel blocks 22 and 23 respectively which constrain arm 5.

The pitch of lead screw 8 is chosen to be $v$ and that of lead screw 9 $\mu$ so that $\mu/v = t (t-s)$. As a result, if detector arm 5 initially points to 6, it will always point to 6 when nuts 20 and 21 are displaced by linked rotation of the lead screws 8 and 9 effected by stepper motor 19 driving spur gears 16, 17 and 18. Since the detector is rigidly connected to arm 5 such that the long axis of the detector is collinear with arm 5, it will always point to 7 which then is the center of rotation of the detector, the crystal being mounted there.

The arc and driving mechanism is oriented relative to the axes of rotation (24) of the arc such that the center of mass of the stepper motor 19 and gear assembly 16, and 17 lies on the rotation axis 24. This arrangement minimizes the dynamic inbalance occurring as the detector is moved about the arc since the heaviest part of the driving mechanism always remains on the axis.

What is claimed is:

1. In a diffractometer for the acquisition of crystallographic data from a single crystal including means to rotatably mount the crystal in the path of a beam of x-rays, an arc mounted on a frame for rotation about a horizontal axis, a detector moveable along said arc, and means to constrain the movement of the crystal and the detector so that the detector is sequentially positioned along a line of the reciprocal lattice of the crystal, the improvement wherein means are provided to constrain translation of the detector on the arc while the arc itself rotates about the horizontal axis said constraining means being a double lead screw arrangement to which the detector is coupled.

2. A diffractometer as claimed in claim 1 in which the lead screws are supported in a frame and are constrained from translation by bearings in the frame.

3. A diffractometer as claimed in claim 2 in which the detector is constrained by members slideable on an arm supporting the detector, said members being coupled for movement to the lead screws.

4. A diffractometer as claimed in claim 3 in which the lead-screws are driven by a common driving means 5. A diffractometer as claimed in claim 4 in which the lead screws each have a pitch such that their ratio is equal $t/(t-s)$ where $t$ is the distance of the lead-screw furtherest from the horizontal axis and $s$ is the distance between the axis of the lead screws.

6. A diffractometer as claimed in claim 5 in which the arm supporting the detector is moveably supported on the arc by rollers rigidly connected to one end of the arm.

* * * * *